United States Patent [19]

Cox et al.

[11] 4,107,314

[45] Aug. 15, 1978

[54] ANTIFUNGAL THIO-ALKYL-IMIDAZOLE DERIVATIVES

[75] Inventors: David A. Cox, Canterbury; Geoffrey E. Gymer, Sandwich, both of England; Braham Shroot, Cachan, France

[73] Assignee: Pfeizer Inc., New York, N.Y.

[21] Appl. No.: 745,305

[22] Filed: Nov. 26, 1976

[30] Foreign Application Priority Data

Dec. 4, 1975 [GB] United Kingdom ............... 49797/75

[51] Int. Cl.² ..................... A61K 31/44; C07D 409/12

[52] U.S. Cl. .............................. 424/263; 260/294.8 D; 260/294.8 G; 260/288 CE; 260/306.8 R; 260/306.8 D; 260/304 R; 260/307 G; 260/308 R; 548/336; 548/341; 544/316; 544/310

[58] Field of Search ................. 260/294.8 G, 294.8 D; 424/263

[56] References Cited

U.S. PATENT DOCUMENTS

| | | | |
|---|---|---|---|
| 3,717,655 | 2/1973 | Godefroi et al. | ..................... 548/336 |
| 4,062,966 | 12/1977 | Gymer | ............................ 424/273 R |

*Primary Examiner*—Alan L. Rotman
*Attorney, Agent, or Firm*—Connolly and Hutz

[57] ABSTRACT

Novel 1-aryl-2-(1-imidazolyl)-alkyl sulphides having anti-fungal properties are disclosed.

13 Claims, No Drawings

ANTIFUNGAL THIO-ALKYL-IMIDAZOLE DERIVATIVES

BACKGROUND OF THE INVENTION

This invention relates to certain novel imidazole derivatives. More particularly, it relates to 1-aryl-2-(1-imidazolyl)-alkyl sulphides which possess anti-fungal activity.

1-($\beta$-aryl)ethyl-imidazole ethers and amines having anti-fungal and anti-bacterial properties are disclosed in U.S. Pat. No. 3,717,655 and British Pat. 1,244,530.

Co-pending U.S. Pat. application Ser. No. 676,104 filed Apr. 12, 1976 now U.S. Pat. No. 4,062,966, assigned to the assignee of the present application and corresponding to Belgian Pat. No. 841,309 discloses antifungal imidazole derivatives, specifically 1-aryl-2-(1-imidazolyl)alkyl ethers and thioethers.

SUMMARY OF THE INVENTION

The present invention provides novel 1-aryl-2(1-imidazolyl)-alkyl-sulphides having the following general formula:

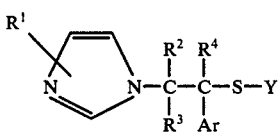
(I)

where
R$^1$, R$^2$, R$^3$ and R$^4$ are each hydrogen or lower alkyl;
Ar is a phenyl group which may optionally be substituted with one or more halogen atoms, lower alkyl groups or lower alkoxy groups; or it may be a thienyl or halothienyl group; and
Y is a mono or bi-cyclic group, containing at least one hetero-atom in a five or six-membered ring and attached to the sulphur atom in formula (I) by a carbon atom of that ring;
and the pharmaceutically-acceptable acid addition salts thereof.

Also disclosed is a composition in dosage unit form useful for the treatment of fungal infections comprising a pharmaceutical carrier containing from about 10 mg. to 3,000 mg. of a compound of formula (I).

In addition there is disclosed a method of treating fungal infections in humans comprising administering to a human subject an effective amount of a compound of formula (I).

In the above and elsewhere in this specification halogen means fluorine, chlorine, bromine or iodine and the term "lower" applied to an alkyl or alkoxy group indicates that such a group contains from 1 to 6 carbon atoms and may be straight or branched chain. Lower alkanoyl groups contain from 2 to 6 carbon atoms and may be straight or branched chain.

The preferred lower alkyl and lower alkoxy groups are methyl and methoxy respectively. The preferred lower alkanoyl group is acetyl. The substituents R$^1$, R$^2$, R$^3$ and R$^4$ are preferably each a hydrogen atom, and the aryl group Ar is preferably a dihalophenyl group, in particular a 2,4-dichlorophenyl group.

The heterocyclic group Y may be an aromatic or non-aromatic group; for example, it may be a thienyl, thiazolyl, thiazolinyl, 2- or 4-imidazolyl, 3-[1,2,4]-triazolyl, thiadiazolyl, oxadiazolyl, 5-tetrazolyl, pyridyl, primidinyl, 2-benzothiazolyl, 2-benzimidazolyl, or a 2-, 3- or 4-quinolyl group, which may optionally be substituted with one or more halogen atoms, or lower alkyl, lower alkoxy, hydroxy, amino, mercapto, lower alkylthio, phenyl, substituted phenyl, aryl-lower alkyl, carboxy, lower alkoxycarbonyl, mono- or di-lower alkyl-amino, lower alkanoylamino, lower alkoxy carbonyl-lower alkyl, aryl-lower alkylamino, carbamoyl, $C_3$–$C_6$ cycloalkyl, nitro, amino-lower alkyl, hydroxy-lower alkyl, lower alkoxycarbonylamino, lower alkylsulphonylamino, amidino, guanidino or ureido groups. Preferred heterocyclic groups are pyridyl (particularly 2-pyridyl optionally substituted by amino and/or chloro or bromo, especially 3-chloro-2-pyridyl, 5-chloro- and 5-bromo-2-pyridyl, 5-amino-2-pyridyl and 5-amino-3-chloro-2-pyridyl), thienyl (particularly 2-thienyl), thiazolyl (particularly 2-thiazolyl and 4,5-dimethyl-2-thiazolyl), imidazolyl (particular 1-methyl-2-imidazolyl)-1,2,4-thiadiazolyl (particularly 3-methyl-1,2,4-thiadiazol-5-yl), and pyrimidinyl (particularly 2-pyrimidinyl).

The preferred aryl substituents, when present in Y, are phenyl and substituted phenyl, preferred substituents on phenyl being hydroxy and halogen.

Particularly preferred individual compounds of the invention include:
1-[2,4-dichloro-$\beta$-(1-methyl-imidazolyl-2-thio)phenethyl]imidazole,
1-[2,4-dichloro-$\beta$-(4,5-dimethylthiazolyl-2-thio)-phenethyl]imidazole,
1-[2,4-dichloro-$\beta$-(2-pyrimidinylthio)phenethyl-]imidazole,
1-[2,4-dichloro-$\beta$-(2-pyridylthio)phenethyl-]imidazole,
1-[2,4-dichloro-$\beta$-(2-thienylthio)phenethyl-]imidazole,
1-[2,4-dichloro-$\beta$-(5-bromopyridyl-2-thio)phenethyl]-imidazole,
1-[2,4-dichloro-$\beta$-(3-methyl-1,2,4-thiadiazolyl-5-thio) phenethyl]imidazole,
1-[2,4-dichloro-$\beta$-(2-thiazolinylthio)phenethyl-]imidazole,
1-[2,4-dichloro-$\beta$-(5-chloro-pyridyl-2-thio)-phenethyl] imidazole,
1-[2,4-dichloro-$\beta$-(3-chloro-pyridyl-2-thio)-phenethyl] imidazole,
1-[$\beta$-(2-pyridylthio)-5-chloro-2-thienyl-ethyl-]imidazole,
1-[2,4-dichloro-$\beta$-(5-aminopyridyl-2-thio)phenethyl] imidazole, and
1-[2,4-dichloro-$\beta$-(5-amino-3-chloro-pyridyl-2-thio) phenethyl]imidazole,
and their pharmaceutically acceptable acid addition salts, particularly their hydrochloride salts.

DETAILED DESCRIPTION OF THE INVENTION

The compounds of the invention may be prepared by reaction of an appropriate 1-aryl-2-(imidazolyl)alkyl halide of the formula:

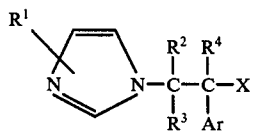
(II)

where Ar and $R^1$ to $R^4$ are as previously defined and X is a halogen atom, preferably chlorine, with a thiol of the formula:

$$Y-SH \qquad (III)$$

where Y is as previously defined.

Compounds in which Y contains a lower alkanoylamino, lower alkoxycarbonylamino or lower alkylsulphonylamino substituent are however preferably prepared by other methods described below.

The reaction of the 1-aryl-2-(imidazolyl)alkyl halide and the thiol is generally performed in an aqueous organic solvent, preferably aqueous dimethyl formamide, in the presence of an acid binding agent, for example, sodium carbonate or bicarbonate or an organic base such as triethylamine. The thiol is usually present in a slight excess. The reaction may be performed at a temperature varying between room temperature and the reflux temperature of the solvent and may take from 1 to 48 hours depending on the particular nature of the reactants and the temperature employed. We have found that the reaction is generally substantially complete within 3 to 4 hours at 100° C or may take up to 48 hours at room temperature. The product may conveniently be isolated from the crude reaction mixture by pouring into water and extracting the mixture with a water immiscible organic solvent for the product, for example diethyl ether, subsequent removal of the organic solvent gives the product frequently as an oil or gum. Alternatively the crude reaction mixture may simply be evaporated and the product extracted with an organic solvent, e.g. ethyl acetate or ether. In either case the crude product may be purified if desired either as the free base or by conversion to an acid addition salt. For example, it may be treated with a solution of hydrogen chloride in ether to give the hydrochloride salt or with a solution of oxalic acid in ether to produce the oxalate salt. The solid product may then be purified, if desired by conventional techniques, for example by recrystallization. The oxalate salt may be converted to a pharmaceutically acceptable acid addition salt, for example, by a conventional ion-exchange technique.

The halides of formula (II) are known compounds described in U.S. Pat. No. 3679697. The thiols of formula (III) are generally known compounds, readily accesible or they may be prepared by well known methods.

Certain compounds of the invention may also be prepared by conversion of one substituent on the group Y into another as follows:

(a) Compounds in which Y contains a lower alkanoylamino substituent may be prepared by the acylation of the corresponding aminosubstituted compound with the appropriate $C_2$-$C_6$ acid chloride or bromide (e.g. $CH_3COCl$ or $CH_3COBr$) or $C_4$-$C_{12}$ acid anhydride (e.g. $[CH_3CO]_2O$);

(b) Compounds in which Y contains a lower alkoxycarbonylamino substituent may be prepared by the reaction of the corresponding amino-substituted compound with the appropriate lower alkyl chloroformate or bromoformate;

(c) Compounds in which Y contains a lower alkylsulphonylamino substituent may be prepared by the reaction of the corresponding amino-substituted compound with the appropriate $C_2$-$C_{12}$ alkane sulphonic anhydride (e.g. $[CH_3SO_2]_2O$) or $C_1$-$C_6$ alkane sulphonyl chloride or bromide (e.g. $CH_3SO_2Cl$);

(d) Compounds in which Y contains an amino substituent may be prepared by reduction of the corresponding nitro-substituted compound, e.g. with ferrous sulphate and ammonia.

(e) Compounds in which Y contains an primary lower alkyl-amino substituent may be prepared by the reaction of the corresponding amino-substituted compound with the appropriate $C_1$-$C_6$ aldehyde, followed by reduction, e.g. with sodium borohydride. This method may be represented as follows:

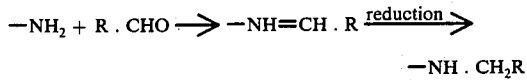

$$-NH_2 + R \cdot CHO \longrightarrow -NH=CH \cdot R \xrightarrow{reduction}$$
$$-NH \cdot CH_2R$$

[R=H or a $C_1$-$C_5$ alkyl group];

and (f) Compounds in which Y contains a ureido substituent may be prepared by reaction of the corresponding amino-substituted compound with sodium or potassium cyanate in the presence of acid.

The compounds of the invention exist in D- and L-optically active isomeric forms and the invention includes these forms as well as the racemic mixtures. The racemic products may be resolved by well known techniques, for example by fractional crystallisation of an addition salt formed with an optically active acid.

Pharmaceutically acceptable acid addition salts of the compounds of the invention are those formed from acids which form non-toxic acid addition salts containing pharmaceutically acceptable anions, such as the hydrochloride, hydrobromide, hydroiodide, sulphate or bisulphate, phosphate or acid phosphate, acetate, maleate, fumarate, nitrate, lactate, tartrate, citrate, gluconate, saccharate and p-toluenesulphonate salts.

The compounds of the invention and their pharmaceutically acceptable acid addition salts are anti-fungal agents, useful in combatting fungal infections in animals, including humans.

The in vitro evaluation of the anti-fungal activity of the compounds has been performed by determining the minimum inhibitory concentration (m.i.c.) of the test compounds in a suitable medium at which growth of the particular micro-organism fails to occur.

In practice a series of agar plates, each having the test compound incorporated at a particular concentration are inoculated with a standard culture of *Candida albicans* and each plate is then incubated for 24 hours at 37° C. The plates are then examined for the presence or absence of growth of the fungus and the appropriate m.i.c. value is noted. Other Micro-organisms used in such tests have included *Cryptococcus neoformans, Aspergillus fumigatus, Trichophyton rubrum, Epidermophyton floccosum, Blastomyces dermatitidis,* and *Torulopsis glabrata.*

The in vivo evaluation of the compounds has also been carried out at a series of dose levels by intraperitoneal or intravenous injection or by oral adminstration, to mice which are inoculated with a strain of *Candida albicans*. Activity is based on the survival of a treated group of mice after the death of an untreated group of mice following 48 hours observation. The dose level at which the compound provides 50% protection against the lethal effect of the infection is noted.

For human use, the anti-fungal compounds of the invention can be administered alone, but will generally be administered in admixture with a pharmaceutical carrier selected with regard to the intended route of administration and standard pharmaceutical practice. For example, they may be administered orally in the form of tablets, containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For oral and parenteral administration to human patients, it is expected that the daily dosage level of the anti-fungal compounds of the invention will be comparable with that of antifungal agents currently in use, e.g. from 0.5 to 50 mg/kg (in divided doses) when administered by the parenteral routes, or from 2 to 200 mg/kg (in divided doses) when administered by the oral route. Thus tablets or capsules of the compounds can be expected to contain from 30 mg to 3 g of active compound for administration orally up to 4 times a day, while dosage units for parenteral administration will contain from 10 mg to 1 g of active compound. The physician in any event will determine the actual dosage which will be most suitable for an individual patient and it will vary with age, the weight and response of the particular patient. The above dosages are exemplary of the average host. There can, of course, be individual cases where higher or lower dosage ranges are merited, and such are within the scope of this invention.

Thus the invention provides a pharmaceutical composition comprising a compound of the formula (I) together with a pharmaceutically-acceptable diluent or carrier.

Alternatively, the anti-fungal compounds of the formula (I) may be applied topically, e.g. in the form of a cream or ointment. For example they may be incorporated into a cream consisting of an aqueous emulsion of polyethylene glycols or liquid paraffin; or they may be incorporated, at a concentration between 1 and 10%, into an ointment consisting of a white wax or white soft paraffin base together with such stabilisers and preservatives as may be required.

The invention also provides an anti-fungal composition for topical administration comprising a compound of the formula (I) together with a topically-acceptable diluent or carrier.

The following are examples of the preparation of the novel compounds of formula (I) according to the invention:

EXAMPLE 1

A solution of sodium carbonate (0.85 g, 8.0 mmole) in water (10 ml) was added to a solution of 1-($\beta$-chloro-2,4-dichlorophenethyl)imidazole hydrochloride (0.82 g, 2.6 mmole) in water (5 ml) and sufficient dimethylformamide was added to give a clear solution (25 ml). 3-Chloro-2-mercapto-pyridine (0.46 g, 3.1 mmole) in dimethylformamide (5 ml) was added and the mixture was stirred at room temperature for 2 days. The solvents were removed under vacuum and the residue was taken up in water (50 ml) and extracted with ether (3 × 50 ml). The combined etherial extracts were dried over magnesium sulphate and evaporated. The oily residue was taken up in dry ether (25 ml) and a solution of hydrogen chloride in ether added to precipitate the hydrochloride salt which was collected by filtration and recrystallised from a mixture of methanol and diisopropyl ether to yield 1-[2,4-dichloro-$\beta$-(3-chloropyridyl-2-thio)phenethyl]imidazole hydrochloride, (0.4 g, 36%), m.p. 225°–226° C. (Found: C, 45.4; H, 3.2; N, 9.8. $C_{16}H_{12}Cl_3N_3S.HCl$ requires C, 45.6; H, 3.1; N, 10.0%).

EXAMPLES 2 – 49

The following 1-(2,4-dichlorophenyl)-2-(1-imidazolyl)ethyl sulphide derivatives were prepared in the same manner as described in Example 1, but starting with 1-$\beta$-chloro-2,4-dichlorophenethyl) imidazole and the appropriate heterocyclic-thiol. Table I shows the structure of the heterocyclic groups Y together with melting points and analytical data. The structures of compounds for which m.p. and analytical data were not obtained were confirmed by i.r. and n.m.r. spectroscopy.

TABLE I

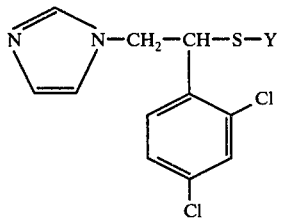

| Ex. No. | Y | Salt | m.p. | Analysis (Theoretical in brackets) C | H | N |
|---|---|---|---|---|---|---|
| 2 | (structure: N-methyl pyrazole) | (HCl)$_2$ | Glass | not obtained | | |
| 3 | (structure: 2-amino-thiadiazole) | HCl | 157–159° | 39.00 (38.21 | 2.76 2.96 | 17.82 17.41) |

TABLE I-continued

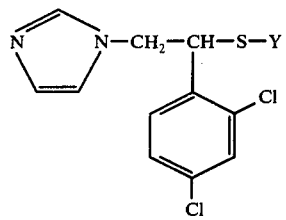

| Ex. No. | Y | Salt | m.p. | Analysis (Theoretical in brackets) C | H | N |
|---|---|---|---|---|---|---|
| 4 | N=C(CH₃)–S–C(CH₃)= (methylvinyl thio) | HCl | Glass | not obtained | | |
| 5 | 2-methylthiazole | HCl | 184.5–185.5° | 41.28 (41.25 | 3.10 3.21 | 13.53 13.74) |
| 6 | pyrimidin-2-yl | HCl | 192–194° | 45.93 (46.48 | 3.42 3.38 | 14.15 14.45) |
| 7 | 1-methyltetrazol-5-yl | Free base | 120–123° | 44.22 (43.93 | 3.44 3.40 | 23.50 23.65) |
| 8 | 1-(4-chlorophenyl)tetrazol-5-yl | HCl | 178° | 43.90 (44.26 | 2.77 2.87 | 16.68 17.21) |
| 9 | 2-acetamido-1,3,4-thiadiazol-5-yl | HCl | Decomposition from 233° | 40.10 (39.99 | 3.20 3.11 | 16.91 15.54) |
| 10 | 5-carboxy-2-acetyl-1,3,4-oxadiazol derivative | 2H₂O | 96+° (dissolves in the water) | 36.75 (39.90 | 3.30 3.30 | 13.66 13.30) |
| 11 | thiazolidinone | HCl | 265–272° | 38.53 (38.09 | 2.73 2.71 | 13.71 13.67) |
| 12 | pyridin-2-yl | CO₂H / CO₂H | 140–145° | 49.09 (49.11 | 3.37 3.43 | 9.25 9.55) |
| 13 | 1H-1,2,4-triazol-3-yl | HCl H₂O | 75–110° | 40.14 (39.57 | 3.24 3.58 | 17.56 17.75) |
| 14 | 2-ethoxy-1,3,4-thiadiazol-5-yl | Free base | Gum | not obtained | | |
| 15 | 1-benzyl-1,2,4-triazol-3-yl | HCl | 190–192° | 48.76 (48.79 | 3.55 3.66 | 18.14 17.97) |

TABLE I-continued

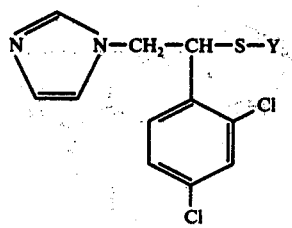

| Ex. No. | Y | Salt | m.p. | C | H | N |
|---|---|---|---|---|---|---|
| | | | | \multicolumn{3}{c}{Analysis (Theoretical in brackets)} | | |
| 16 | (imidazolyl-O-cyclopropyl structure) | CO₂H / CO₂H | 88–90° | 43.61 (43.52 | 3,49 3.55 | 10.97 11.28) |
| 17 | (tetrazole-phenyl structure) | (CO₂H / CO₂H)₂ | 94–95° | 44.58 (44.22 | 3.02 3.01 | 13.40 14.07) |
| 18 | (pyridyl) | (CO₂H / CO₂H)₂ | 147–149° | 44.63 (45.30 | 3.17 3.23 | 7.78 7.92) |
| 19 | (imidazolyl-dichlorophenyl) | (CO₂H / CO₂H)₂ | 167–168° | 47.03 (47.66 | 3.08 2.81 | 10.42 10.59) |
| 20 | (imidazole NH) | (H₂O)₁ | 124–126° | 49.58 (48.91 | 3.57 3.67 | 16.52 16.30) |
| 21 | (thienyl) | HCl | 159–161° | 45.88 (45.98 | 3.36 3.35 | 7.22 7.15) |
| 22 | (dimethyl SCH₂CH₃ pyrimidine) | HCl | 197–199.5° | 46.52 (46.80 | 4.16 4.15 | 12.17 12.15) |
| 23 | (quinoline) | Free base | 133–135° | 59.71 (59.98 | 3.76 3.78 | 10.66 10.50) |
| 24 | (thiazole-CO₂CH₂CH₃) | CO₂H / CO₂H | 160–163° | 44.30 (44.03 | 3.35 3.31 | 8.19 8.12) |
| 25 | (imidazole-CO₂CH₂CH₃-C₆H₅) | HCl | 194–195° | 52.41 (52.73 | 3.96 4.05 | 10.95 10.70) |
| 26 | (thiazole-CH₂-phenyl) | HCl | 189–192° | 49.03 (49.18 | 3.34 3.38 | 10.08 10.43) |
| 27 | (bis-pyrimidinyl-dimethyl) | (HCl)₂ | 217–220° | 45.19 (45.25 | 3.87 3.97 | 12.29 12.08) |
| 28 | (pyrimidinyl-methyl) | (HCl)₂ | 130–133° | 44.27 (43.86 | 3.69 3.68 | 13.18 12.79) |

TABLE I-continued

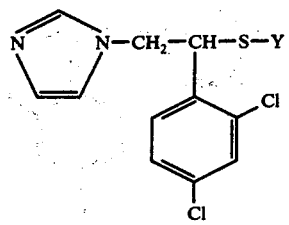

| Ex. No. | Y | Salt | m.p. | Analysis (Theoretical in brackets) C | H | N |
|---|---|---|---|---|---|---|
| 29 | [triazole-SH group] | HCl | 260–265° | 37.24 (36.65 | 2.95 2.60 | 13.13 13.16) |
| 30 | [imidazoline-CH₂CO₂CH₂CH₃ group] | CO₂H CO₂H | 100° | 40.72 (44.19 | 3.56 3.68 | 12.45* 13.57) |
| 31 | [5-bromopyridin-2-yl] | Free base | 144° | 44.85 (44.75 | 2.91 2.80 | 9.79 9.79) |
| 32 | [benzothiazol-2-yl] | HCl | 196–197° | 45.16 (45.31 | 2.81 2.75 | 9.05 8.81) |
| 33 | [4-(4-hydroxyphenyl)thiazol-2-yl] | CO₂H CO₂H | 170–171° | 48.84 (49.07 | 3.32 3.19 | 7.72 7.81) |
| 34 | [pyridin-3-yl] | CO₂H CO₂H ¼ (CH₃OH) | 90–92° | 48.54 (48.88 | 3.61 3.60 | 9.45 9.37) |
| 35 | [4-phenyl-thiazol-2-yl] | CO₂H CO₂H | 148–151° | 48.18 (48.20 | 3.04 3.08 | 10.62 10.71) |
| 36 | [benzimidazol-2-yl] | Free base | 197–200° | 54.57 (54.54 | 3.71 3.63 | 14.43 14.39) |
| 37 | [4-methylthiazol-2-yl] | CO₂H CO₂H | 130–140° | 42.27 (41.67 | 3.19 3.06 | 12.03 12.15) |
| 38 | [4,5-dihydrothiazol-2-yl] | CO₂H CO₂H | 148–150° | 42.62 (42.86 | 3.28 3.37 | 9.26 9.38) |
| 39 | [thiazol-2-yl] | HCl | 176–180° | 42.51 (42.83 | 3.04 3.08 | 10.94 10.70) |
| 40 | [5-chloropyridin-2-yl] | HCl | 147–149° | 45.36 (45.64 | 3.11 3.11 | 10.11 9.98) |
| 41 | [pyrimidin-2-yl] | Free base | 149–150° | 51.8 (51.3 | 3.5 3.4 | 16.2 16.0) |
| 42 | [5-nitropyridin-2-yl] | Free base | 213–215° | 49.4 (48.6 | 3.1 3.1 | 14.1 14.2) |

TABLE I-continued

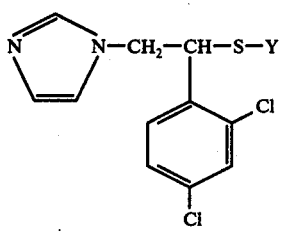

| Ex. No. | Y | Salt | m.p. | Analysis (Theoretical in brackets) C | H | N |
|---|---|---|---|---|---|---|
| 43 | pyridyl-COOH | Free base | 199–203° | 52.2 (51.8 | 3.4 3.3 | 10.4 10.6) |
| 44 | H₂N-pyridyl | 3HCl | glass | characterised by n.m.r. and mass spectra | | |
| 45 | pyridyl-CONH₂ | HCl | 247–252° | 46.3 (47.5 | 3.2 3.5 | 12.3 13.0) |
| 46 | pyridyl-NHCH₂-phenyl-OH | oxalate | glass | characterised by n.m.r. and mass spectra | | |
| 47 | Cl-pyridyl-NO₂ | Free base | 156° | 44.9 (44.7 | 2.4 2.6 | 11.4 13.0) |
| 48 | NH₂-pyridyl-Br | 1½ tartrate | glass | 39.3 (39.5 | 3.6 3.3 | 8.2 8.4) |
| 49 | Cl-pyridyl-Cl | HCl | 228–230° | 40.8 (42.1 | 2.8 2.6 | 9.3 9.2) |

*impurity present

EXAMPLE 50

2-Mercapto-pyridine (0.77 g, 7.0 mmole) was dissolved in aqueous sodium carbonate solution (1.5 g in 70 ml) and added to a solution of 1-(β-chloro-phenethyl)-imidazole hydrochloride (1.5 g, 6.0 mmole) in dimethylformamide (70 ml). The mixture was stirred overnight at room temperature and then poured into water (300 ml) and extracted with ether (4 × 100ml). The combined etherial extracts were washed with water and brine, dried over magnesium sulphate and evaporated. The oily product was taken up in dry ether and a saturated solution of oxalic acid in ether added to precipitate the oxalate salt as a gum which solidified on trituration with dry ether. Recrystallisation from methanol and ether gave 1[β-(2-pyridyl-thio)phenethyl]imidazole dioxalate (0.38 g, 14%), m.p. 128° C. (Found: C, 54.9; H, 4.55; N, 9.6. $C_{16}H_{15}N_3S.(C_2H_2O_4)_2$ requires C, 54.8; H, 4.3; N, 10.1%).

EXAMPLE 51

A mixture of 1(2-chloro-5-thienyl)-2-)1-imidazolyl)-ethyl chloride (1.5 g, 5.3 mmole), 2-mercapto-pyridine (0.75 g, 6.7 mmole) and sodium carbonate (2 g, 19 mmole) in dry dimethylformamide (100 ml) was stirred at room temperature for 5 hours. The solution was filtered and the organic solvent removed under vacuum. The residual oil was taken up in ethyl acetate, filtered and a saturated solution of oxalic acid in ether added. The precipitated oxalate salt was collected by filtration, washed with ether and recrystallised from a mixture of acetone, methanol and di-isopropyl ether to yield 1 -[β-(2-pyridylthio) -5-chloro-2-thienyl-ethyl-]imidazole oxalate (0.98 g, 46%), m.p. 190°–191° C. (Found: C, 46.6; H, 3.5; N, 10.1. $C_{16}H_{12}ClN_3S.C_2H_2O_4$ requires C, 46.7; H, 3.4; N, 10.2%).

EXAMPLE 52

Ferrous sulphate (240 g) was dissolved in water (600 ml), and concentrated hydrochloric acid (1 ml) and 1-[2,4-dichloro-β-(5-nitropyridyl-2-thio)phenethyl]imidazole (22.5 g, - prepared as in Example 42) were then added to the solution. The resulting mixture was vigorously stirred and heated at 90°, and "0.88" ammonia (100 ml followed by 3 × 50 ml at 2 minute intervals) was added. The mixture was then heated at 90° for 40 minutes.

The reaction mixture was then cooled, diluted with water, and the iron-containing residue filtered off. The filtrate was extracted with ethyl acetate, separated, and the organic phase was dried and treated with a saturated solution of d-tartaric acid in methanol, yielding, as a precipitate, which was filtered off, 1-[2,4-dichloro-β-(5-aminopyridyl-2-thio)phenethyl] imidazole bis-tartrate (1.5 g - crop 1). The iron residue was then stirred in ethyl acetate, and the ethyl acetate phase was decanted, dried and treated with a solution of d-tartaric acid in methanol to precipitate a further crop (22 g - crop 2) of the desired product. The iron residue was then treated a further time with ethyl acetate/d-tartaric acid in methanol to yield a final crop (crop 3 - 3 g) of the product. The crops were combined and dried to a fine hygroscopic powder, m.p. 75°-85°, (yield 26 g - 68%).

Analysis %: Found: C, 44.40; H, 4.34; N, 8.15. Calculated for $C_{16}H_{14}N_4SCl_2.2HOOC.(CHOH)_2.COOH$: C, 43.32; H, 3.94; N, 8.42.

By a similiar procedure to the above, but using a solution of oxalic acid in ether in place of a solution of d-tartaric acid in methanol, 1-[2,4-dichloro-β-(5-aminopyridyl-2-thio)phenethyl]imidazole mono-oxalate, m.p. 105°-125°, was prepared.

Analysis %: Found: C, 47.83; H, 3.71; N, 11.63. Calculated for $C_{16}H_{14}N_4Cl_2S.C_2H_2O_4$: C, 47.49; H, 3.54; N, 12.31.

EXAMPLE 53

1-[2,4-dichloro-β-(3-chloro-5-aminopyridyl-2-thio)phenethyl] imidazole monohydrochloride, m.p. 222°-224°, was prepared by a procedure similar to that of Example 52, starting from the corresponding 3-chloro5-nitropyridyl imidazole and using hydrogen chloride in ether in place of tartaric acid in methanol.

Analysis %: Found: C, 44.1; H, 3.2; N, 12.5. Calculated for $C_{16}H_{13}N_4SCl_3.HCl$: C, 44.0; H, 3.2; N, 12.8.

EXAMPLE 54

An aqueous solution of 1-[1,4-dichloro-β-(5-aminopyridyl-2-thio)phenethyl]imidazole bis-tartrate (2.5 g - prepared as in Example 52) was treated with aqueous sodium carbonate solution, and extracted with methylene chloride. After separation, the organic phase was dried (MgSO₄) filtered, and the solvent removed under reduced pressure. The resulting residue of the free base was taken up in 30% aqueous acetic acid and an aqueous solution of sodium cyanate (containing 0.5 g of cyanate) was added dropwise. The resulting mixture was left at room temperature overnight, and further sodium cyanate (0.25 g) was then added and the reaction mixture stirred overnight at room temperature. Further sodium cyanate (0.25 g) was then added and the reaction mixture allowed to stand for 24 hours. The reaction mixture was then basified with aqueous sodium carbonate solution, and extracted with ethyl acetate. After separation, the organic phase was dried (MgSO₄), and the solvent was removed under reduced pressure. The resulting residue was taken up in a minium of methanol and chromatographed on a silica column, the desired product, 1-[2,4-dichloro-β-(5-ureidopyridyl-2-thio)phenethyl] imidazole, being eluted with ethyl acetate/methanol. The yield of the desired product was 225 mg, melting at 106°-110°. The product was characterised by n.m.r., i.r. and mass spectral data.

EXAMPLE 55

An aqueous solution of 1-[2,4-dichloro-β-(5-aminopyridyl-2-thio)phenethyl]imidazole bis-tartrate (1.5 g) (prepared as in Example 52) was treated with aqueous sodium carbonate solution, and extracted with methylene chloride. After separation, the organic phase was dried (MgSO₄), filtered and evaporated to dryness under reduced pressure. The resulting residue of the free base was taken up in tetrahydrofuran, and triethylamine (0.5 ml) and methane sulphonic anhydride (0.44 g) were then added, the reaction mixture then being stirred at room temperature overnight. An additional portion of the anhydride (80 mg) was added, and the resulting mixture was again stirred at room temperature overnight. A further portion of the anhydride (80 mg) was then added, and the reaction mixture again stirred at room temperature overnight. The reaction mixture was then evaporated to dryness under reduced pressure, and water and a small quantity of aqueous sodium carbonate solution was then added to take up the residue. The resulting mixture was extracted with ethyl acetate, dried (MgSO₄), and the solvent removed under reduced pressure. The residue was taken up in a small quantity of ethyl acetate and a saturated solution of oxalic acid in ether was added. The precipitate of 1-[2,4-dichloro-β-(5-methylsulphonylamino-pyridyl-2-thio) phenethyl]imidazole mono-oxalate was filtered and recrystallised from MeOH.Et₂O. The yield of the product, m.p. 141°-3°, was 270 mg.

Analysis %: Found: C, 43.52; H, 3.53; N, 10.62. Calculated for $C_{17}H_{16}N_4O_2S_2Cl_2.(COOH)_2$: C, 42.78; H, 3.38; N, 10.50.

EXAMPLE 56

Compounds prepared in the Examples above have been tested for anti-fungal activity by the methods previously described. The in vitro m.i.c. values against *Candida Albicans* $C_{66}$ are given in Table II.

TABLE II

| Example | m.i.c. (μg/ml) | Example | m.i.c. (μg/ml) |
|---------|----------------|---------|----------------|
| 1  | 6.25 | 27 | 12.5 |
| 2  | 6.25 | 28 | 12.5 |
| 4  | 6.25 | 31 | 6.25 |
| 5  | 12.5 | 32 | 25 |
| 6  | 6.25 | 33 | 25 |
| 7  | 50   | 36 | 25 |
| 8  | 3.1  | 37 | 3.1 |
| 9  | 25   | 38 | 12.5 |
| 10 | 25   | 39 | 6.25 |
| 11 | 12.5 | 40 | 6.25 |
| 12 | 1.6  | 41 | 12.5 |
| 13 | 50   | 44 | 25 |
| 14 | 6.25 | 45 | 50 |
| 15 | 3.1  | 46 | 50 |
| 16 | 12.5 | 47 | 25 |
| 17 | 6.25 | 48 | 6.25 |
| 18 | 50   | 49 | 25 |
| 21 | 6.25 | 50 | 12.5 |
| 22 | 12.5 | 51 | 3.1 |
| 23 | 25   | 52 | 6.25 |
| 24 | 12.5 | 53 | 6.25 |
| 25 | 50   | 54 | 50 |

TABLE II-continued

| Example | m.i.c. (μg/ml) | Example | m.i.c. (μg/ml) |
| --- | --- | --- | --- |
| 26 | 6.25 | | |

What is claimed is:

1. A compound of the formula:

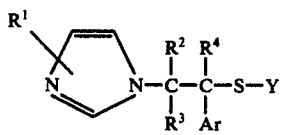

and the pharmaceutically-acceptable acid addition salts thereof wherein $R^1$, $R^2$, $R^3$ and $R^4$ are each hydrogen or alkyl of from 1 to 6 carbon atoms;

Ar is thienyl, halothienyl, phenyl, mono- or disubstituted phenyl, said substituents being selected from halogen, lower alkyl or lower alkoxy;

and Y is pyridyl, monosubstituted or disubstituted pyridyl, wherein said substituents are selected from amino, chloro and bromo.

2. A compound as claimed in claim 1 wherein Y is selected from 2-pyridyl, 3-chloro-2-pyridyl, 5-chloro-2-pyridyl, 5-bromo-2-pyridyl, 5-amino-2-pyridyl, 5-amino-3-chloro-2-pyridyl.

3. A compound as claimed in claim 2 wherein $R^1$, $R^2$, $R^3$ and $R^4$ are each hydrogen and Ar is dihalophenyl.

4. A compound as claimed in claim 3 wherein Ar is 2,4-dichloro-phenyl.

5. 1-[2,4-dichloro-β-(2-pyridylthio)phenethyl] imidizole.

6. 1-[2,4-dichloro-β-(5-bromopyridyl-2-thio)-phenethyl] imidazole.

7. 1-[2,4-dichloro-β-(5-chloro-pyridyl-2-thio)-phenethyl] imidazole.

8. 1-[2,4-dichloro-β-(3-chloro-pyridyl-2-thio)-phenethyl] imidazole.

9. 1-[β-(2-pyridylthio)-5-chloro-2-thienyl-ethyl] imidazole.

10. 1-[2,4-dichloro-β-(5-aminopyridyl-2-thio)-phenethyl] imidazole.

11. 1-[2,4-dichloro-β-(5-amino-3-chloro-pyridyl-2-thio) phenethyl]imidazole.

12. A pharmaceutical composition for treatment of fungal infections in animals comprising a pharmaceutically-acceptable diluent or carrier and an antifungal effective amount of a compound as claimed in claim 1.

13. A method of treating fungal infections in animals which comprises parenterally, orally or topically administering to an animal in need of such treatment an antifungal effective amount of a compound as claimed in claim 1.

* * * * *

UNITED STATES PATENT AND TRADEMARK OFFICE
CERTIFICATE OF CORRECTION

PATENT NO. : 4,107,314
DATED : August 15, 1978
INVENTOR(S) : David A. Cox et al

It is certified that error appears in the above–identified patent and that said Letters Patent are hereby corrected as shown below:

In the covering page of the above patent, left hand column, in the line entitled "[73] Assignee:" change "Pfeizer Inc." to --Pfizer Inc.--.

Signed and Sealed this

Twenty-seventh Day of March 1979

[SEAL]

Attest:

RUTH C. MASON
Attesting Officer

DONALD W. BANNER
Commissioner of Patents and Trademarks